(12) United States Patent
Schertiger et al.

(10) Patent No.: US 10,299,956 B2
(45) Date of Patent: May 28, 2019

(54) EXPANDABLE COLLECTING BAG FOR AN OSTOMY APPLIANCE

(71) Applicant: Coloplast A/S, Humlebaek (DK)

(72) Inventors: Lars Olav Schertiger, Fredensborg (DK); Mads Hindhede Svanegaard, Bagsvaerd (DK); Annalie Marie Rikovitz Joergensen, Copenhagen (DK); Hans Falleboe, Gentofte (DK)

(73) Assignee: Coloplast A/S, Humlebaek (DK)

( * ) Notice: Subject to any disclaimer, the term of this patent is extended or adjusted under 35 U.S.C. 154(b) by 222 days.

(21) Appl. No.: 15/325,115

(22) PCT Filed: Jul. 10, 2015

(86) PCT No.: PCT/DK2015/050210
§ 371 (c)(1),
(2) Date: Jan. 10, 2017

(87) PCT Pub. No.: WO2016/004959
PCT Pub. Date: Jan. 14, 2016

(65) Prior Publication Data
US 2017/0156918 A1    Jun. 8, 2017

(30) Foreign Application Priority Data

Jul. 10, 2014  (DK) ................................ 2014 70431
Sep. 1, 2014   (DK) ................................ 2014 00492

(51) Int. Cl.
*A61F 5/44*   (2006.01)
*A61F 5/445*  (2006.01)
*A61F 5/448*  (2006.01)

(52) U.S. Cl.
CPC ............ *A61F 5/445* (2013.01); *A61F 5/4407* (2013.01); *A61F 5/448* (2013.01)

(58) Field of Classification Search
CPC ......... A61F 5/4407; A61F 5/445; A61F 5/448
See application file for complete search history.

(56) References Cited

U.S. PATENT DOCUMENTS

| | | | | |
|---|---|---|---|---|
| 3,279,331 A | * | 10/1966 | Platt ....................... | B65D 33/18 |
| | | | | 383/120 |
| 3,780,739 A | * | 12/1973 | Frank .................... | A61F 5/4405 |
| | | | | 604/335 |
| 4,445,898 A | * | 5/1984 | Jensen .................... | A61F 5/441 |
| | | | | 604/332 |
| 2003/0023210 A1 | | 1/2003 | Bedard et al. | |

(Continued)

FOREIGN PATENT DOCUMENTS

| | | |
|---|---|---|
| CN | 102917673 A | 2/2013 |
| DE | 19752598 C1 | 8/1999 |

(Continued)

*Primary Examiner* — Kai H Weng
(74) *Attorney, Agent, or Firm* — Coloplast Corp., Coloplast A/S; Nick Baumann

(57) ABSTRACT

An expandable collecting bag is provided. The collecting bag can be used in an ostomy appliance and has a cap portion and an expandable portion. The expandable portion is folded inside the cap portion with the outer surfaces facing each other. The cap portion is folded over and envelopes the expandable portion with the inner surfaces facing each other. A method for producing a collecting bag is also provided.

12 Claims, 5 Drawing Sheets

(56) References Cited

U.S. PATENT DOCUMENTS

| | | | |
|---|---|---|---|
| 2003/0073962 A1 | 4/2003 | Olsen et al. | |
| 2010/0217214 A1 | 8/2010 | Hansen et al. | |
| 2011/0028923 A1* | 2/2011 | Murray | A61F 5/4405 604/332 |
| 2012/0302981 A1* | 11/2012 | Lam | A61F 5/445 604/344 |
| 2013/0253455 A1 | 9/2013 | Masters et al. | |

FOREIGN PATENT DOCUMENTS

| | | |
|---|---|---|
| DE | 20212695 U1 | 1/2003 |
| EP | 2668935 A1 | 12/2013 |
| RU | 2008144401 A | 5/2010 |
| WO | 02102289 A1 | 12/2002 |
| WO | 2007115575 A1 | 10/2007 |
| WO | 2009124324 A1 | 10/2009 |
| WO | 2013/142577 A1 | 9/2013 |

\* cited by examiner

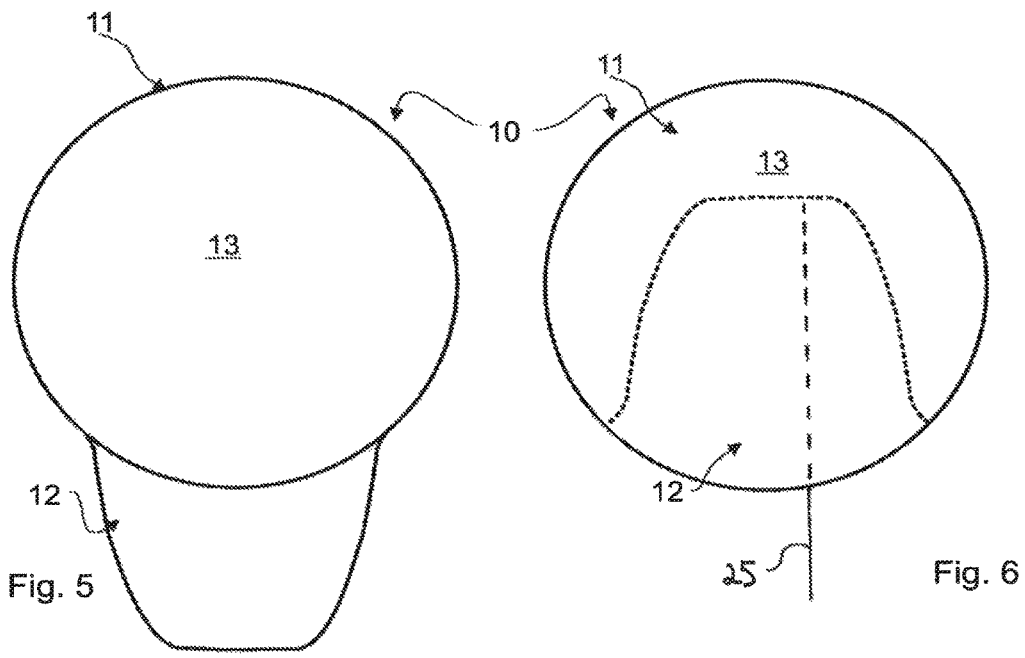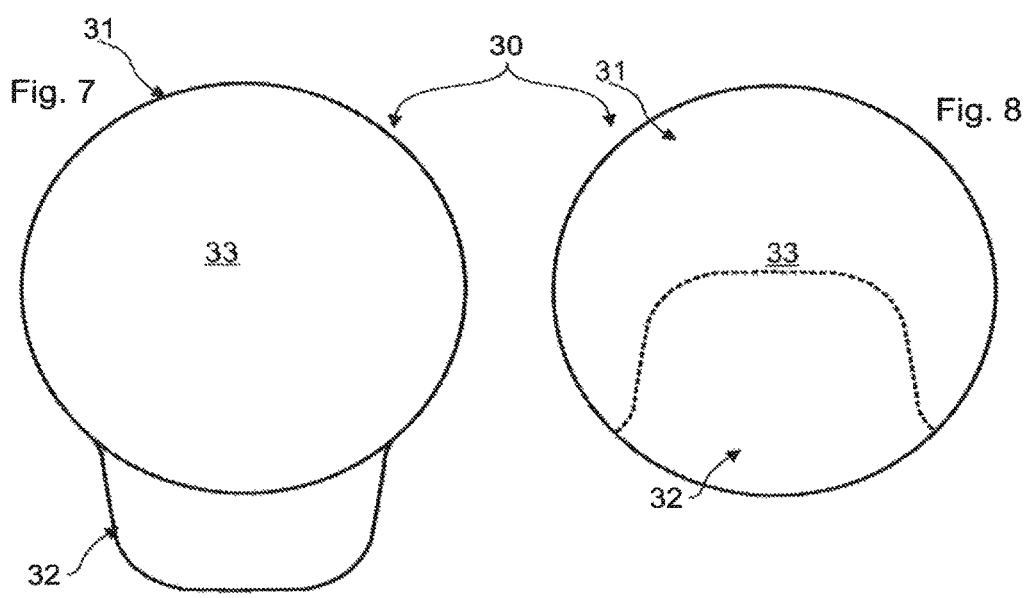

EXPANDABLE COLLECTING BAG FOR AN OSTOMY APPLIANCE

The invention relates to an expandable collecting bag that can be used in an ostomy appliance.

BACKGROUND

In connection with surgery for a number of diseases in the gastro-intestinal tract, one of the consequences in many cases is that the patient is left with an abdominal stoma, such as a colostomy, an ileostomy or a urostomy in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time.

An ostomy appliance may be in the form of a one-piece appliance for which a collecting bag for human body wastes is permanently, or fixedly, secured to an adhesive base plate for attachment to the human skin. Alternatively, the ostomy appliance may be a two-piece appliance comprising a base plate and a collecting bag which may be coupled to and uncoupled from each other through a coupling means. This has the effect that the base plate does not need to be separated from the skin of the user as often as exchange of the collecting bag requires. The base plate may need only to be changed every third or fourth day depending on the user, whereas the collecting bag may be changed more than once per day. Typically, it is desirable to need as few exchanges of the base plate as possible in order to reduce the risk of skin complications.

Collecting bags may be provided in different sizes depending on the desired use. For example, larger bags may be used at night, whereas smaller bags may be used when discretion is needed. In some situations—e.g. during exercise—the use of so-called stoma caps may be preferred. Stoma caps are small collecting bags just covering the base plate and the stoma. However, since the discharge from the stoma cannot be regulated at will, a user wearing a stoma cap may need a collecting volume of a size exceeding the volume of the cap.

DESCRIPTION OF RELATED ART

WO2013/142577 describes an expandable ostomy pouch and an expandable ostomy cap, which include a first portion and a second portion sharing a common cavity. The first portion and the second portion are configured such that the second portion can be inverted and inserted within the first portion in a compacted state. The second portion can be manually pulled out or can be expanded due to gravity and/or due to elevated pressure with the pouch due to the stomal discharge, as the cavity is filled with stomal discharge.

SUMMARY OF THE INVENTION

The invention relates to an expandable collecting bag for an ostomy appliance. The collecting bag may for example be of the stoma cap with an expandable portion. The edges of the expandable portion of the collecting bag are attached to each other with the outer surfaces facing each other, and the cap portion of the collecting bag envelopes the expandable portion, and the edges of the cap portion are attached to each other with the inner surfaces facing each other. Thereby the expandable portion will have a natural tendency to be folded up inside the cap portion and, furthermore, the cap portion will be thin and discreet because of the edges of the expandable portion being folded with the outer surfaces facing each other.

BRIEF DESCRIPTION OF THE DRAWING

In FIG. 1, the expandable collecting bag is shown in a non-expanded configuration.

In FIG. 2, the expandable collecting bag is shown in an expanded configuration.

FIG. 5 illustrates a front view of the same expandable collecting bag as in FIGS. 1 and 2. In FIG. 5, the expandable collecting bag is shown in an expanded configuration.

FIG. 6 illustrates a front view of the same expandable collecting bag as in FIGS. 1, 2 and 5. In FIG. 6, the expandable collecting bag is shown in a non-expanded configuration.

FIGS. 7 and 8 illustrate front views of another embodiment of an expandable collecting bag.

DETAILED DESCRIPTION OF THE INVENTION

Figure 1:
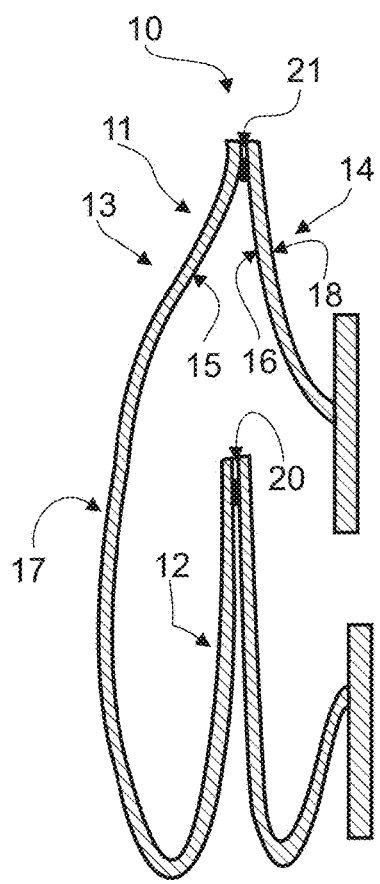
FIG. 1 illustrates a cross-sectional view of an expandable collecting bag for an ostomy appliance.

In a first aspect, the invention relates to an expandable collecting bag for an ostomy appliance comprising a cap portion and an expandable portion, the collecting bag having at least two configurations, a non-expanded and an expanded configuration, where in the expanded configuration, the cap portion and the expandable portion constitute one continuous collecting cavity with inner surfaces facing the continuous collecting cavity and outer surfaces facing outwards, the edges of the expandable portion being attached to each other with the outer surfaces facing each other and the edges of the cap portion being folded over and enveloping the expandable portion with the inner surfaces facing each other.

An expandable collecting bag for an ostomy appliance as described above will have a natural tendency to be folded up, because the edges of the expandable portion is being attached to each other with the outer surfaces facing each other and the edges of the cap portion is folded over and attached to each other with the inner surfaces facing each other. Therefore, the collecting bag will be thin and discreet in the non-expanded configuration due to the fact that there will be only two layers of foil materials at the edge of the expandable portion. Furthermore, because of the natural tendency of the expandable portion to be folded up, the risk of unintended expansion of the expandable portion is minimized or even eliminated, whereas expansion by gravity or by the user pulling at the expandable portion is possible.

In the following, whenever referring to the proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user, and the distal side is the opposite side—the side furthest away from the user during use.

The axial direction is defined as the direction of the stoma, when the appliance is worn by a user. Thus the axial direction is substantially perpendicular to the abdominal surface of the user. The thickness of the collecting bag is in the axial direction.

The longitudinal direction is defined as the direction from the top towards the bottom of the collecting bag when an ostomy appliance including the collecting bag is worn by a user. The length of the collecting bag is in the longitudinal direction and the width is in the direction transverse to the longitudinal direction.

An ostomy appliance is well-known in the art. The ostomy appliance may be in the form of a stoma cap, which is also well-known in the art. The collecting bag of the ostomy appliance usually comprises a front wall on the distal side and a rear wall on the proximal side. The walls are made of gas—and liquid impermeable foil—material (for example of polyethylene (PE), polyvinyl-chloride (PVC) or ethylene-vinyl-acetate (EVA)) which is welded at the edges or the rim. The waste inlet opening is provided in the rear wall.

The collecting bag may be mentioned as being folded up when it is in a non-expanded configuration and likewise the collecting bag may be mentioned as being un-folded when it is in an expanded configuration.

The front wall and the rear wall both have an inner surface and an outer surface, the inner surfaces facing inwards towards the collecting volume and the outer surfaces facing outwards. Thus, the inner surfaces of the collecting bag correspond to the inner surfaces of the front wall and rear wall, respectively, and the outer surfaces of the collecting bag correspond to the outer surfaces of the front wall and rear wall, respectively.

In an embodiment of the invention, the collecting bag includes a portion of absorbing material inside the collecting bag. This absorbing material may be, e.g., synthetic crimped fibre materials of polyolefin, absorbing foams or sponge-like material as well as super-absorbing materials, such as hydro-gel-forming polymeric material. The material may be used to absorb some of the liquid output exiting the stoma and thus makes the cleaning process easier when the collecting bag is to be exchanged for another. In a related embodiment, the absorbing material may be positioned towards the bottom of the cap portion, in which case the material may assist in expanding the bag as the bag is filling due to the weight of the bag. The material may also be loosely arranged within the bag.

In an embodiment of the invention, the expandable portion is provided with a pulling strip 25 of any suitable material. This strip 25 (FIG. 6) may be attached to the portion during the production, e.g., at the welding, and may serve the purpose of allowing the user to expand the collecting bag by pulling at the strip 25. The strip 25 may protrude at the lower edge of the cap portion in the non-expanded configuration of the collecting bag, so that it is easier to grasp.

In an embodiment of the invention, the cap portion is generally circular with a diameter of less than 100 mm. The expandable portion may alternatively be generally quadrangular with a length in the longitudinal direction of the collecting bag of less than 100 mm and a width of less than 60 mm.

Another aspect of the invention relates to a method of producing an expandable collecting bag for an ostomy appliance comprising a cap portion and an expandable portion, the collecting bag having at least two configurations, a non-expanded and an expanded configuration, the method comprising the steps of a. providing foil blanks of a size and shape corresponding to the finished front and rear wall of the collecting bag
b. providing a waste-inlet opening in the rear wall of the collecting bag
c. placing the foil blanks so that the surfaces of the foil blanks that will face outwards in the finished collecting bag face each other
d. attaching edges of the expandable portion to each other
e. folding the foil blanks of the cap portion over and enveloping the expandable portion so that the surfaces facing inwards in the finished collecting bag face each other
f. attaching the edges of the cap portion to each other This method provides for a thin and discreet expandable collecting bag as described above.

In an embodiment, the foil blanks corresponding to the finished front wall include an upper part and a lower part attached to each other and the foil blanks corresponding to the finished rear wall include an upper part and a lower part attached to each other.

In an embodiment, the method includes welding as the attachment of the edges to each other.

DETAILED DESCRIPTION OF THE DRAWING

FIGS. 1-2 and 5-6 illustrate an expandable collecting bag 10 for an ostomy appliance according to an embodiment of the invention. The expandable collecting bag 10, seen in cross-section in FIGS. 1 and 2 and from the front in FIGS. 5-6, has a cap portion 11 and an expandable portion 12. The cap portion is generally circular and the expandable portion is generally quadrangular. The collecting bag is made of two foils constituting a distal front wall 13 and a proximal rear wall 14 of the collecting bag in the expanded configuration. The foils also constitute the cap portion and the expandable portion and has inner surfaces 15, 16 and outer surfaces 17, 18 of the front and rear wall respectively. The inner surfaces together form a continuous collecting cavity 19 in the expanded configuration. The expandable portion 12 is welded along its edges 20 with the outer surfaces 17, 18 facing each other. The cap portion 11 is also welded along its edges 21 but with the inner surfaces 15, 16 facing each other.

Figure 3:
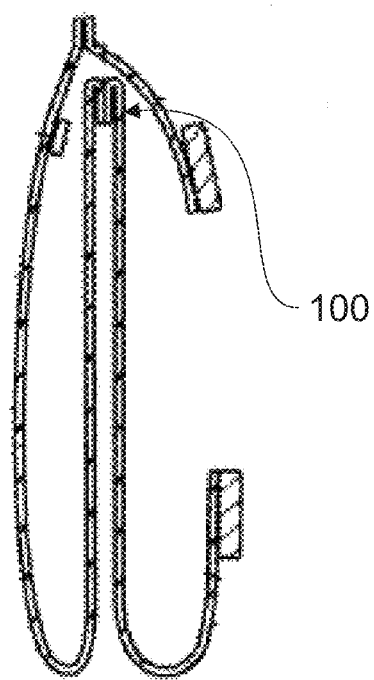
FIG. 3 illustrates a prior art expandable collecting bag.

The non-expandable configuration is thin and discreet because the edges of the expandable portion (see FIG. 1) will only have the two foil blanks facing each other as opposed to the prior art collecting bag of FIG. 3, where the edges 100 of the folded up portion have four layers due to the fold inside the collecting bag.

Figure 2:
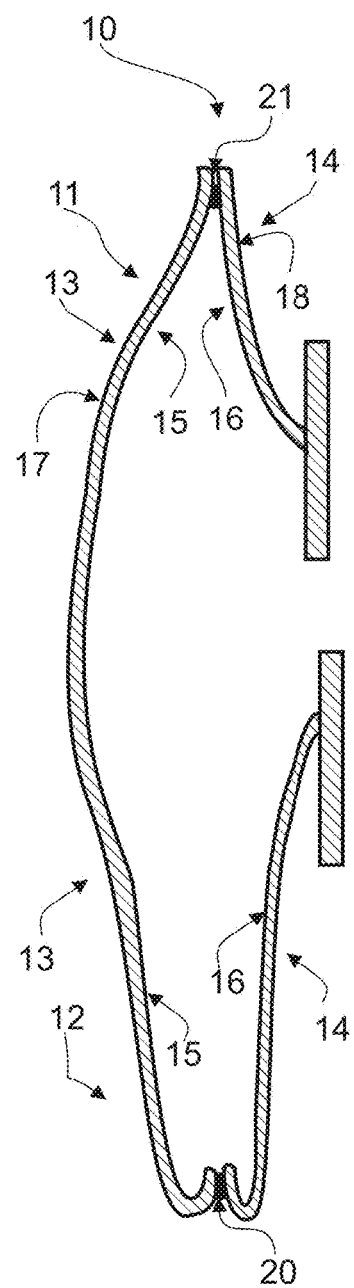
FIG. 2 illustrates a cross-sectional view of the same expandable collecting bag as in FIG. 1.
Figure 4:
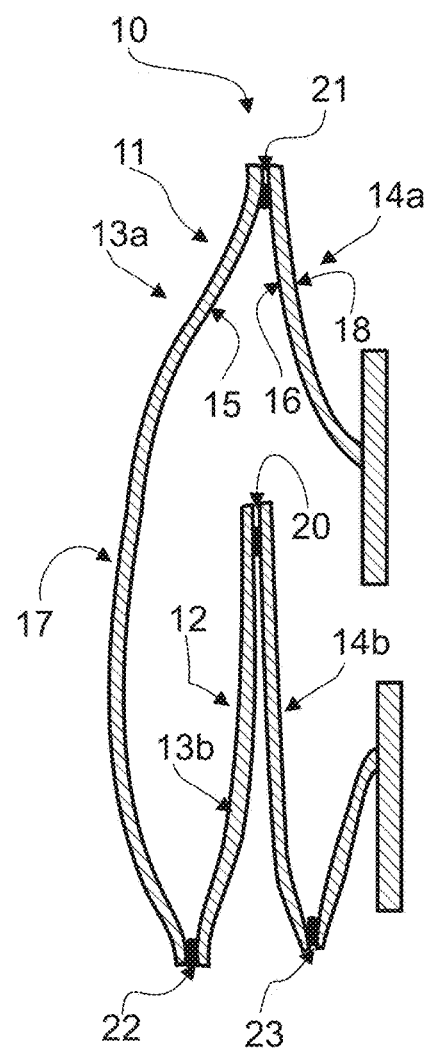
FIG. 4 illustrates a cross-sectional view of another embodiment of an expandable collecting bag for an ostomy appliance, the expandable collecting bag being shown in a non-expanded configuration.

FIG. 4 illustrates an alternative embodiment. The only difference with respect to FIGS. 1 and 2 is that in the embodiment of FIG. 4 the front wall consists of two parts, an upper 13a part and a lower part 13b, which are welded together at 22. Likewise, the rear wall consists of two parts, an upper part 14a and a lower part 14b, welded together at 23. A front and rear wall of two parts may be even more prone to be folded, due to the welds provided at 22 and 23.

FIGS. 7 and 8 illustrate an embodiment of a collecting bag 30 similar to the one of FIGS. 1,2, 5 and 6. However, in this embodiment, the expandable portion 32 is rather small compared to the one in FIGS. 1, 2, 5 and 6. FIGS. 7 and 8 illustrate the embodiment seen from the front so only the front wall 33 can be seen in the figures. FIG. 7 illustrates the collecting bag 30 in an expanded configuration and FIG. 8 illustrates the collecting bag 30 in a non-expanded configuration, with the expandable portion 32 folded inside the cap portion 31, shown in dimmed lines.

Figures 9, 10:
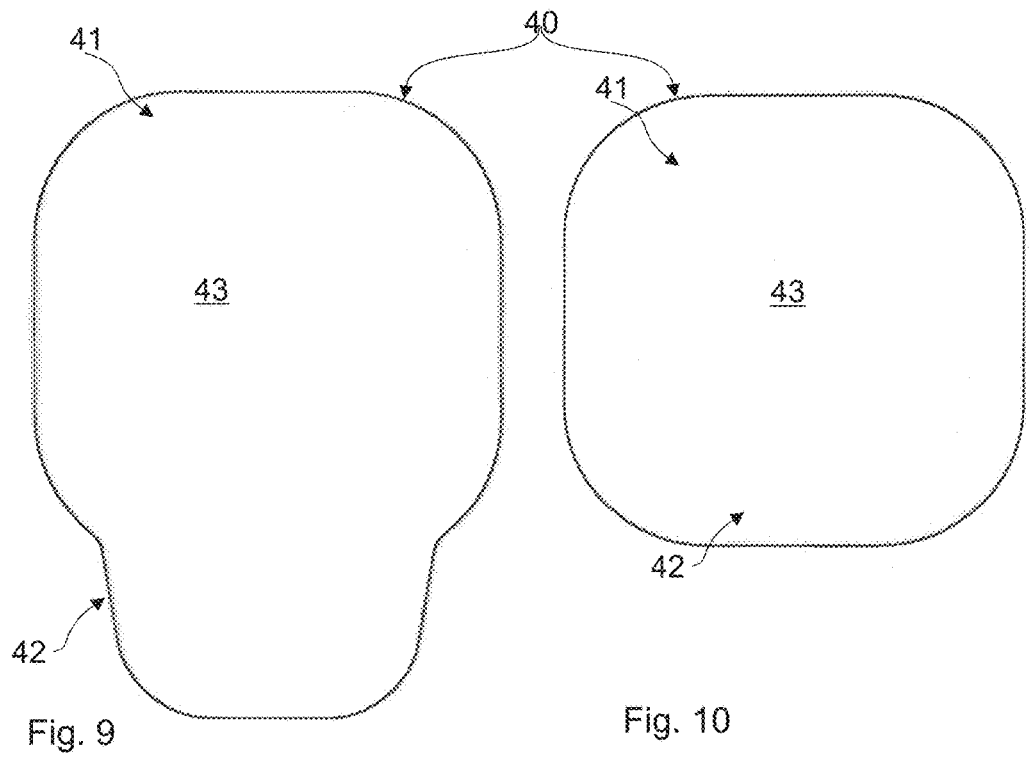
FIGS. 9 and 10 illustrate front views of a third embodiment of an expandable collecting bag.

FIGS. 9 and 10 illustrate an embodiment of a collecting bag 40 that differs from the collecting bag 30 of FIGS. 7 and 8 in that the cap portion 41 is quadrangular. FIGS. 9 and 10 also illustrate the embodiment seen from the front, so only the front wall 43 can be seen in the figures. FIG. 9 illustrates the collecting bag 40 in an expanded configuration and FIG. 10 illustrates the collecting bag in a non-expanded configuration, with the expandable portion (not shown) folded inside the cap portion 41.

Figures 11, 12:
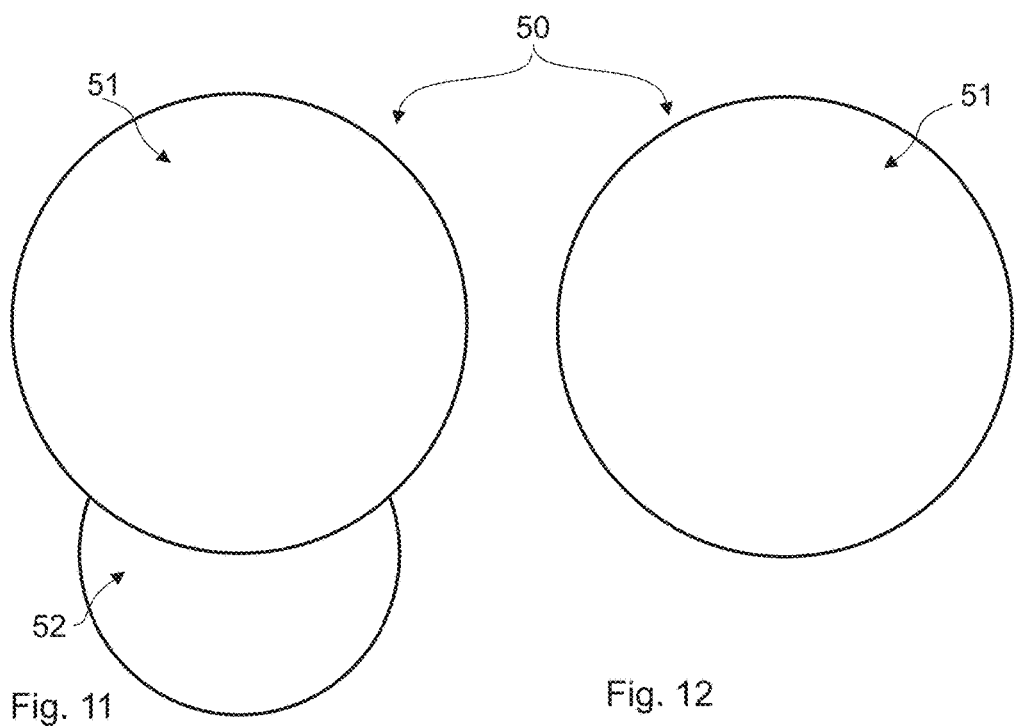
FIGS. 11 and 12 illustrate front views of a fourth embodiment of an expandable collecting bag.

In the embodiment shown in FIGS. 11 and 12, the collecting bag 51 has a circular cap portion 51 and a semicircular expandable portion 52. FIGS. 11 and 12 illustrate the embodiment seen from the front, so only the front wall 53 can be seen in the figures. FIG. 11 illustrates the collecting bag 50 in an expanded configuration and FIG. 12 illustrates the collecting bag 50 in a non-expanded configuration, with the expandable portion (not shown) folded inside the cap portion 51.

Other embodiments, e.g., other combinations of quadrangular and circular shapes, are also within the scope of this invention. Other shapes of the expandable portion and cap portion may also be contemplated. The only limit is that the expandable portion must be able to be contained within the boundaries of the cap portion so that the edges of the expandable portion does not protrude beyond the edges of the cap portion.

The invention claimed is:

1. An expandable collecting bag for an ostomy appliance, the collecting bag comprising:
    a front wall and a rear wall;
    a base plate secured to the rear wall with a waste inlet opening formed in both of the base plate and the rear wall, with the rear wall attached to the front wall to form a cap portion and an expandable portion, the collecting bag is adapted to transition to an expanded configuration when waste is collected in the collecting bag;
    wherein the cap portion and the expandable portion combine to form a collecting cavity with a first inner surface of the front wall and a second inner surface of the rear wall forming an interior of the collecting cavity, and with a first outer surface of the front wall and a second outer surface of the rear wall facing outwards forming an exterior of the collecting bag;
    characterized in that the expandable portion has a sealed edge defined by the first outer surface of the front wall in direct attachment to the second outer surface of the rear wall, and characterized in that the cap portion has the first inner surface of the front wall in direct attachment to the second inner surface of the rear wall;
    wherein, in a non-expanded configuration, the expandable collecting bag has a discreet profile in which the sealed edge of the expandable portion is folded into a perimeter of the cap portion, and a stored thickness of the sealed edge located between the base plate and the front wall is limited to a thickness of the rear wall plus a thickness of the front wall.

2. The expandable collecting bag as claimed in claim 1, wherein the collecting bag further includes a portion of absorbing material inside the collecting cavity of the collecting bag.

3. The expandable collecting bag as claimed in claim 2, wherein the absorbing material is loosely arranged inside the collecting cavity of the collecting bag.

4. The expandable collecting bag as claimed in claim 2, wherein the absorbing material is located in the cap portion in the non-expanded configuration.

5. The expandable collecting bag as claimed in claim 1, wherein the expandable portion is provided with a pulling strip.

6. The expandable collecting bag as claimed in claim 5, wherein the pulling strip protrudes beyond the perimeter of the cap portion in the non-expanded configuration.

7. The expandable collecting bag as claimed in claim 1, wherein the cap portion is circular with a diameter of less than 100 mm.

8. The expandable collecting bag as claimed in claim 1, wherein the expandable portion is quadrangular with a length in a longitudinal direction of the collecting bag of less than 100 mm and a width of less than 60 mm.

9. The expandable collecting bag of claim 1, wherein the front wall and the rear wall are provided as foil blanks of a size and shape that are adapted to form the collecting bag after the rear wall is attached to the front wall.

10. The expandable collecting bag of claim 1, wherein the direct attachment is welding welded joint.

11. The expandable collecting bag as claimed in claim 1, wherein the cap portion is generally circular and the expandable portion is generally quadrangular, and in the non-expanded configuration, the generally quadrangular expandable portion is folded into the generally circular cap portion.

12. The expandable collecting bag as claimed in claim 1, wherein, in the non-expanded configuration, the discreet profile of the expandable collecting bag is provided by the expandable portion having a longitudinal length of less than 100 mm that is folded into a generally circular cap portion having a diameter of less than 100 mm.

* * * * *